(12) United States Patent
Hommann

(10) Patent No.: US 7,370,759 B2
(45) Date of Patent: May 13, 2008

(54) DEVICE FOR TEMPORARILY RETAINING A PROTECTIVE NEEDLE CAP OF AN INJECTION APPARATUS

(75) Inventor: Edgar Hommann, Grossaffoltern (CH)

(73) Assignee: TecPharma Licensing AG, Burgdorf (CH)

( * ) Notice: Subject to any disclaimer, the term of this patent is extended or adjusted under 35 U.S.C. 154(b) by 174 days.

(21) Appl. No.: 11/132,732

(22) Filed: May 19, 2005

(65) Prior Publication Data

US 2005/0279664 A1    Dec. 22, 2005

Related U.S. Application Data

(63) Continuation of application No. PCT/CH03/00756, filed on Nov. 17, 2003.

(30) Foreign Application Priority Data

Nov. 25, 2002 (CH) ................................ 1985/02

(51) Int. Cl.
*A61M 5/32* (2006.01)
(52) U.S. Cl. .................. 206/365; 206/364; 604/192
(58) Field of Classification Search ............ 206/364, 206/365, 366; 604/192, 263
See application file for complete search history.

(56) References Cited

U.S. PATENT DOCUMENTS

| 4,915,233 A | 4/1990 | Smith |
| 5,356,385 A * | 10/1994 | Latini ..................... 604/110 |

FOREIGN PATENT DOCUMENTS

| DE | 29608141 U1 | 8/1996 |
| EP | 0838228 A | 4/1998 |
| FR | 2714836 | 7/1995 |
| NL | 1006153 C | 12/1998 |
| WO | WO 00/51667 | 9/2000 |

* cited by examiner

*Primary Examiner*—Mickey Yu
*Assistant Examiner*—Jerrold Johnson
(74) *Attorney, Agent, or Firm*—David E. Bruhn

(57) ABSTRACT

A device and method for removing and replacing a needle-protecting cover associated with an injection apparatus, the device comprising a housing, a receptacle in the housing for accommodating the injection apparatus, and a holding mechanism, wherein the receptacle is movable in the housing and, in a first position of the receptacle, the holding mechanism is in a releasing position and, in a second position of the receptacle, the holding mechanism is in a holding position.

11 Claims, 2 Drawing Sheets

DEVICE FOR TEMPORARILY RETAINING A PROTECTIVE NEEDLE CAP OF AN INJECTION APPARATUS

CROSS-REFERENCE TO RELATED APPLICATION(S)

This application is a Continuation of International Application No. PCT/CH2003/000756, filed on Nov. 17, 2003, which claims priority to Swiss Application No. 1985/02, filed on Nov. 25, 2002, the contents of which are incorporated by reference herein in their entirety.

BACKGROUND

The invention relates to an devices and methods for temporarily or releasably coupling, connecting or attaching components. More particularly, it relates to apparatus and methods for the temporary removal, retaining and replacing of a protective needle cap of an injection apparatus, wherein the apparatus comprises a housing, a receptacle part arranged in the housing for accommodating the injection apparatus, and holding means.

Needle protectors, shields or caps are known in many embodiments. With typical, manually operated injection syringes the protective needle cap, as a rule, is removed by hand before use and after use is replaced by hand. In doing this, there exists for a user a considerable danger of injury from the used injection needle. For this reason, aids have already been proposed for removal and especially for replacement of the protective cap, all of which, however, require a separate operational step.

It would be advantageous if a protective needle cap could be removed and afterwards be replaced through a process step that is a step or part of the preparation, handling and/or use of an injection device.

SUMMARY

In one embodiment, the present invention comprises comprising a housing, a receptacle and a holding mechanism, wherein the receptacle is movable in the housing, and wherein in a first state of the receptacle part the holding mechanism is in a releasing position, and in a second state of the receptacle part the holding mechanism is in a holding position.

In one embodiment, the present invention comprises a device and method for removing and replacing a needle-protecting cover associated with an injection apparatus, the device comprising a housing, a receptacle in the housing for accommodating the injection apparatus, and a holding mechanism, wherein the receptacle is movable in the housing and, in a first position of the receptacle, the holding mechanism is in a releasing position and, in a second position of the receptacle, the holding mechanism is in a holding position.

According to one embodiment of the present invention, the receptacle part is movable by rotation from its first state into its second state. This solution is advantageous especially for injection devices that are taken apart by rotation for the purpose of inserting and removing a syringe or the like. The holding mechanism, also referred to as holding means, is simultaneously actuated by this rotation.

According to another embodiment of the invention, the holding means are formed as clamping pieces that, pivoting around pivot axes running parallel to the longitudinal axis of the apparatus, can pivot against the longitudinal axis. This permits a simple construction of the apparatus. When, according to other embodiments of the invention, the receptacle part contains a pressing curve and, if need be, a releasing curve, a forced control of the clamp parts results, which enables safe operation of the apparatus.

In one embodiment, the present invention comprises a curved sleeve rotatable by a certain angle within a housing, wherein an injection apparatus comprising a protective needle cap placed thereon is inserted into the sleeve so as to join a forward part of the injection apparatus to a drive part of the injection apparatus. The sleeve, which partially rotates along with the injection apparatus and presses in clamping pieces by means of a curved section when the injection apparatus is twisted or turned, the clamping pieces retaining the protective needle cap. After being used, the injection apparatus is inserted back into the curved sleeve and twisted in the opposite direction to be disassembled, the protective needle cap thereby being released to be removed together with a portion of the injection apparatus.

According to another embodiment of the invention, and indicator or indicator means are provided that make visible from outside the injection device the rotational position in which the receptacle part is situated. The indicator preferably comprises a window in the housing, through which a different marking is visible at this marking region in each rotational position of the receptacle. These measures make the operation of the apparatus still more convenient and secure.

Another aspect of the invention relates to a loading station for the preparation of an injection apparatus, the station containing an apparatus according to the invention. The loading station can include other functional elements that serve the preparation of an injection apparatus, for example an autoinjector. In one embodiment, the apparatus according to the invention is preferably removably accommodated in the loading station. One embodiment of the loading station provides a case for storing and carrying the apparatus and parts of an injector apparatus. This enables the user of an injection apparatus to easily carry the necessary individual parts with him and to store them in a clearly-arranged manner.

DETAILED DESCRIPTION

Figure 1:
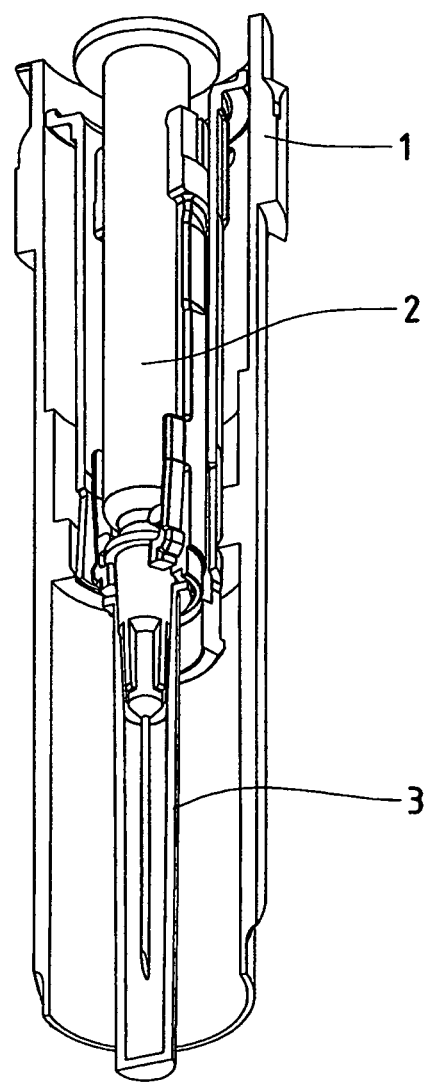
FIG. 1 is a cutaway perspective view of a forward part of an autoinjector.
Figure 2:
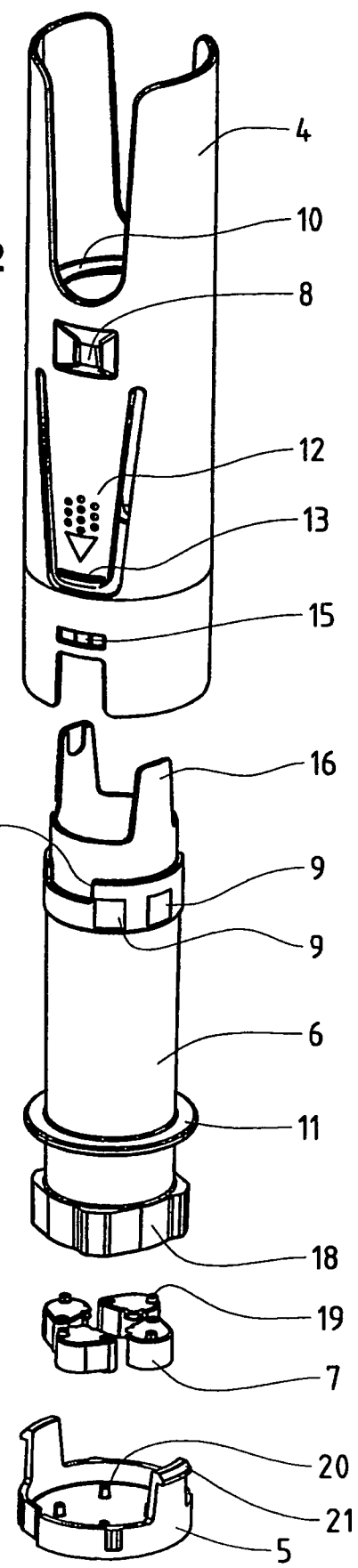
FIG. 2 is an exploded view of an exemplary embodiment of the present invention.
Figure 3:
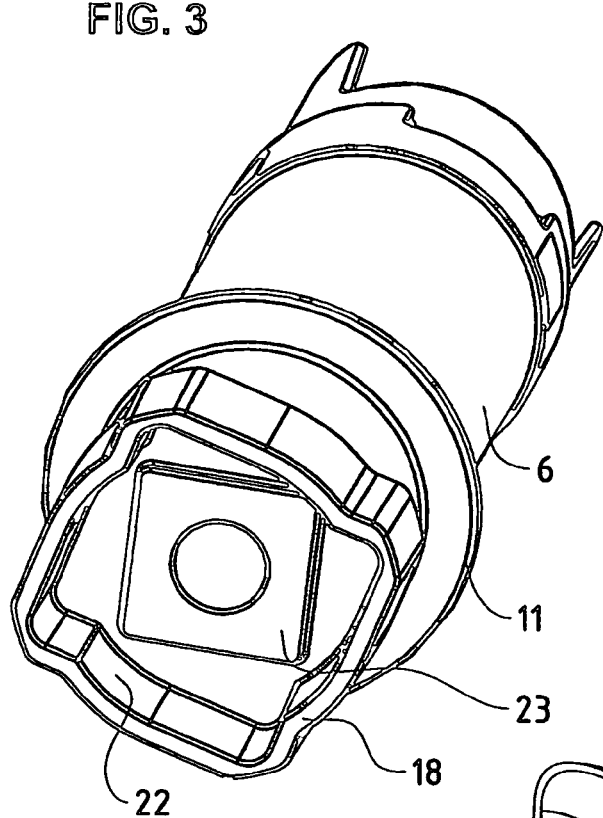
FIG. 3 is a perspective view of a detail of FIG. 2.

Represented in FIG. 1, for the better understanding of the context of the present invention, is the forward part 1 of an autoinjector with a syringe 2 accommodated therein. Before use of the autoinjector, the forward part 1 is combined by means of a bayonet-type connection with a drive part (not shown) that contains functional elements, in particular springs, for the automatic carrying out of an injection. The injection needle associated with the syringe 2 is covered in a known way by a protective needle cap 3 placed on it. The apparatus according to the present invention serves to remove the protective needle cap 3 before the use of the autoinjector and to replace the cap after the use of the autoinjector. For this purpose, the present invention respectively utilizes the processes of the assembly and disassembly of the autoinjector before and after an injection.

The apparatus 30 shown in FIGS. 2-5 comprises a housing 4, which is closed at the bottom by a housing bottom 5 that is held by means of stop lobes 21, the latter engaging the opening 15 of the housing 4. Held in a rotatable manner in the housing 4 is a generally cylindrically shaped, curved receiving sleeve 6. The sleeve's ability to rotate is limited by stops 17 arranged on the curved sleeve 6, which stops works together with a rib on the housing 4 (the rib not being visible in the figures). A window 8 arranged or formed in the housing 4, corresponding in each case to the state of rotation of the curved sleeve 6, permits a view of one of the two, preferably colored, marking regions 9 provided on the curved sleeve. An inner flange 10 arranged in the upper region of the housing 4 supports the curved sleeve 6 radially as well as axially, and in the lower region of the curved sleeve 6 an outer flange 11 is provided, with which the curved sleeve 6 is guided radially in the housing 4. The curved sleeve accommodates, in its interior, the forward part 1 of an autoinjector. Tabs 16 projecting upward and/or ribs (not shown) provided in the interior of the curved sleeve 6 ensure a rotationally-fixed connection between the curved sleeve 6 and the forward part 1 of the autoinjector.

Figure 4:
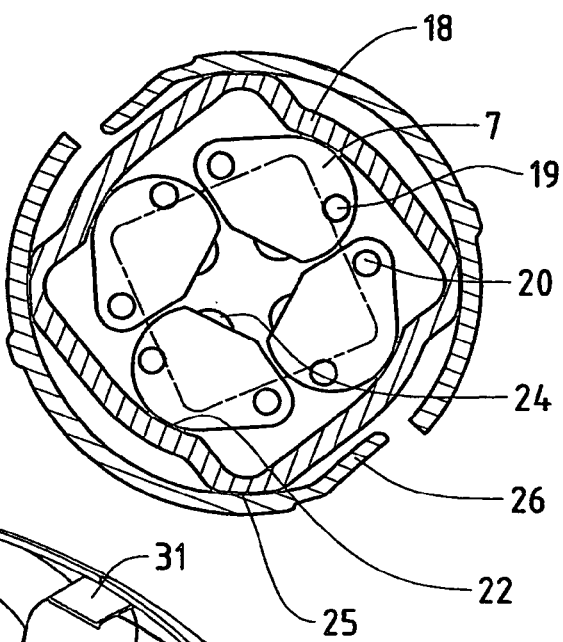
FIG. 4 is a cross-section through a lower part of the apparatus according to FIG. 2.

From the housing bottom 5, four bearing pins 20 project upwards, on which four clamping pieces 7 are rotatably supported. These clamp pieces 7 grip and firmly hold the protective needle cap 3 when the autoinjector is put together, conversely releasing the protective needle cap 3 when the autoinjector is taken apart for the purpose of removing a spent syringe 2. As shown in FIG. 4, gripping ribs 24 are provided on the clamping pieces 7, which ribs are pressed into the relatively soft material of the protective needle cap 3 in order to grip these securely. The movement of the clamping pieces 7 is controlled in part by a curved part 18 formed below on the curved sleeve 6. Inside the curved part is located a pressing curve 22, which presses the clamping pieces 7 inward, when the curved sleeve 6 is rotated in the clockwise sense. This is seen best in FIG. 4. If the curved sleeve 6 is rotated in the counter-clockwise sense, a release curve 23 (seen best in FIG. 3) arranged inside the pressing curve 22 acts on control pins 19, which are arranged protruding or extending upwardly on each clamp piece 7, and presses the clamping pieces 7 outwardly. The curved part 18 of the curved sleeve 6 is guided with its outer circumference 25 in the housing bottom 5, tongues 26 formed on the housing bottom 5 working together with the outer region 25 in such a way that the curved sleeve 6 clicks into its two rotational end states.

For use of the apparatus, it is either held firmly in one hand or advantageously set into an corresponding loading station 27, as this is described further below. Then the forward part 1 of an autoinjector is placed from above into the curved sleeve 6 and a syringe filled with an agent and having an injection needle and protective needle cap 3 is stuck into the forward part 1. Then the driving part of the autoinjector is placed on and rotated in the clockwise sense. With this rotation—simultaneously or one after another, each according the friction between the individual components—the drive part of the autoinjector is coupled to the forward part 1 by way of the mentioned bayonet connection and the curved sleeve 6 is rotated in housing 4, wherein the clamping pieces 7 are forced inward by the pressing curve 22 and the protective needle cap 3 is clamped tightly between them. Visible now in window 8 is a different, for example, green colored region 9, which signals that the autoinjector is now ready for operation and can be withdrawn upward, whereby the protective needle cap 3 remains clamped between the clamping pieces 7. After the injection, the process plays out in a reversed sequence, the autoinjector being stuck with its the forward part 1 into the curved sleeve 6, the injection needle sliding into the protective needle cap 3, and the operating part of the autoinjector being rotated in the counter-clockwise sense, in order to release its connection with the forward part 1. In this rotation, the curved sleeve is carried along and the release curve 23 ensures that the clamping pieces 7 release the protective needle cap. Finally, the syringe 2 together with the replaced protective needle cap 3 is removed from the forward part 1.

Figure 5:
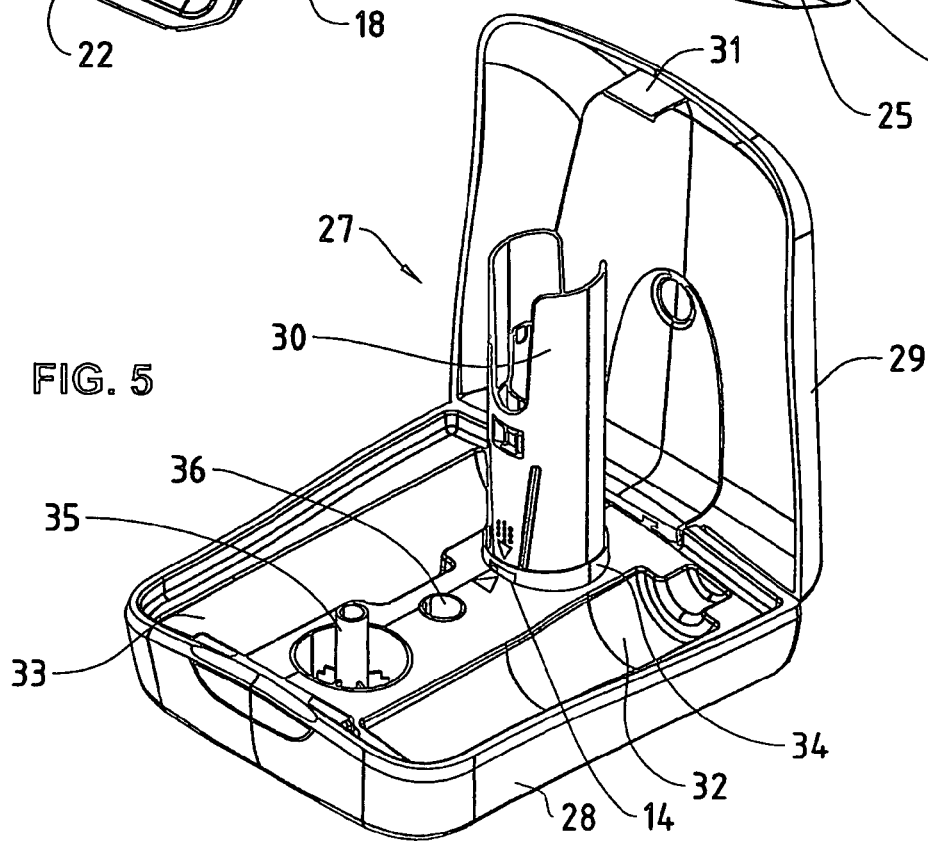
FIG. 5 depicts a loading station with an apparatus according to FIG. 2.

FIG. 5 shows a loading station 27 for an autoinjector, in which station the above described apparatus 30 is held in the use position. Present in the housing 4 of the apparatus are suitable catch structures 12, such as elastic tongues, with catch nibs 13, which snap into catch recesses 14 provided in a receptacle 34 of the loading station 27. The loading station in the depicted example is, at the same time, a case consisting of a lower part 28, a cover 29 and a lock 31. Besides the described receptacle 34 for the apparatus 30, the illustrated example includes a receptacle 32 for the drive part of the autoinjector, a second receptacle 33 for the apparatus, a stressing pin 35 for stressing the springs of the autoinjector, and another receptacle 36 for a tool such as a key for tightening and loosening an injection needle of the Luer-lock or other type.

While various embodiments, including preferred embodiments, of the present invention have been described herein, it is contemplated that various modifications could be made without deviating from the spirit of the present invention. Accordingly, it is intended that the scope of the present invention be dictated by the appended claims.

The invention claimed is:

1. A device for removing and replacing a needle-protecting cover associated with an injection apparatus, the device comprising a housing, a generally elongated cylindrical sleeve in the housing for accommodating at least a portion of the injection apparatus, and a plurality of clamping pieces, wherein the generally elongated cylindrical sleeve is movable in the housing and, in a first position, is in a releasing position and, in a second position, is in a holding position.

2. An apparatus for temporary retaining of a protective needle cap of an injection apparatus, comprising a housing, a generally elongated cylindrical sleeve arranged in the housing for accommodating the injector apparatus, and a plurality of clamping pieces, wherein the generally elongated cylindrical sleeve is movable in the housing, so that in a first state of the generally elongated cylindrical sleeve the clamping pieces are in a releasing position and in a second state of the generally elongated cylindrical sleeve the clamping pieces are in a holding position.

3. An apparatus according to claim 2, wherein the generally elongated cylindrical sleeve is rotatably movable from the first state to the second state.

4. An apparatus according to claim 3, wherein the clamping pieces are moveable around pivot axes extending parallel to a longitudinal axis of the apparatus.

5. An apparatus according to claim 4, wherein the generally elongated cylindrical sleeve comprises a pressing curve that in the second rotational state of the generally elongated cylindrical sleeve presses the clamping pieces toward the longitudinal axis of the apparatus.

6. An apparatus according to claim 5, wherein the generally elongated cylindrical sleeve comprises a releasing curve that in the first rotational state of the generally elongated cylindrical sleeve presses the clamping pieces away from the longitudinal axis of the apparatus.

7. An apparatus according to claim 2, further comprising indicator means making the rotational state of the generally elongated cylindrical sleeve part visible from the outside.

8. An apparatus according to claim 7, wherein the indicator means comprises a window in the housing, through which, in each rotational state of the generally elongated cylindrical sleeve, a different marking region associated with the generally elongated cylindrical sleeve is visible.

9. A loading station for the preparation of an injection apparatus, and a device for removing and replacing a needle-protecting cover associated with the injection apparatus, the device comprising a generally elongated cylindrical sleeve for accommodating at least a portion of the injection apparatus, and a plurality of clamping pieces, wherein the generally elongated cylindrical sleeve is movable in a housing and, in a first position, is in a releasing position and, in a second position, is in a holding position.

10. A loading station according to claim 9, wherein the device is removably accommodated in the loading station.

11. A loading station according to 10, wherein the station comprises means for storing parts of the injection apparatus.

* * * * *